(12) United States Patent
Oldenbandringh et al.

(10) Patent No.: US 11,645,901 B2
(45) Date of Patent: May 9, 2023

(54) INTRUSION DETECTORS FOR LORRIES

(71) Applicant: Contained Technologies UK Limited, London (GB)

(72) Inventors: Henk Oldenbandringh, Soest (NL); Josh Lopez, Kuraba Point (AU); Alex Szymborski, Ashampstead (GB)

( * ) Notice: Subject to any disclaimer, the term of this patent is extended or adjusted under 35 U.S.C. 154(b) by 0 days.

(21) Appl. No.: 17/170,877

(22) Filed: Feb. 8, 2021

(65) Prior Publication Data

US 2021/0280038 A1 Sep. 9, 2021

(51) Int. Cl.
| G08B 21/12 | (2006.01) |
| G01N 33/00 | (2006.01) |
| G08B 13/00 | (2006.01) |
| G08B 25/10 | (2006.01) |

(52) U.S. Cl.
CPC ........... *G08B 21/12* (2013.01); *G01N 33/004* (2013.01); *G08B 13/00* (2013.01); *G08B 25/10* (2013.01)

(58) Field of Classification Search
CPC ........ G08B 21/12; G08B 13/00; G08B 25/10; G01N 33/004
See application file for complete search history.

(56) References Cited

U.S. PATENT DOCUMENTS

| 7,659,816 | B2* | 2/2010 | Wandel | G08B 13/08 |
| | | | | 340/541 |
| 2006/0170537 | A1* | 8/2006 | Marriott | G08B 21/22 |
| | | | | 340/426.24 |
| 2006/0187022 | A1* | 8/2006 | Dawson | H04B 3/542 |
| | | | | 340/538.11 |
| 2007/0133356 | A1* | 6/2007 | O'Connor | G08B 25/016 |
| | | | | 368/243 |
| 2007/0216537 | A1* | 9/2007 | Park | G04C 21/34 |
| | | | | 340/691.1 |
| 2008/0252450 | A1* | 10/2008 | Wandel | B65D 55/026 |
| | | | | 340/541 |
| 2009/0303052 | A1* | 12/2009 | Aklepi | G06Q 10/08 |
| | | | | 340/573.2 |
| 2010/0163731 | A1* | 7/2010 | Haran | G08B 21/22 |
| | | | | 250/340 |
| 2010/0265069 | A1* | 10/2010 | Michaels | G08B 13/08 |
| | | | | 340/572.3 |
| 2011/0133925 | A1* | 6/2011 | Hummer | G08B 25/012 |
| | | | | 340/539.1 |
| 2014/0180953 | A1* | 6/2014 | Westcott | A23B 7/148 |
| | | | | 705/332 |
| 2017/0254581 | A1* | 9/2017 | Kamei | A23B 7/148 |
| 2019/0195845 | A1* | 6/2019 | Kim | G01N 33/0075 |
| 2020/0026253 | A1* | 1/2020 | Fuhr | G05B 19/0423 |
| 2020/0053651 | A1* | 2/2020 | Lee | G06F 21/32 |

(Continued)

*Primary Examiner* — Ojiako K Nwugo
(74) *Attorney, Agent, or Firm* — Miller IP Law

(57) ABSTRACT

According to an aspect of intrusion detectors for lorries, there is provided a method of detecting intrusion of one or more persons into cargo hold of a vehicle carrying goods that emit carbon dioxide the method comprising identifying an intrusion event by detecting a decrease in concentration of carbon dioxide within the cargo hold. For example, the intrusion evident may be identified by detecting a decrease in concentration of carbon dioxide within the cargo hold of at least 400 ppm. A decrease in $CO_2$ can be attributed to unauthorised access being made into the cargo hold as cargo holds typically remain closed during a journey.

12 Claims, 2 Drawing Sheets

(56) References Cited

U.S. PATENT DOCUMENTS

2020/0278741 A1* 9/2020 Madhusudhana ...... H04R 29/00
2020/0284945 A1* 9/2020 Khan ..................... G08B 5/22
2021/0137467 A1* 5/2021 Aoki .................... A61B 5/7235

* cited by examiner

INTRUSION DETECTORS FOR LORRIES

CROSS-REFERENCE TO RELATED APPLICATIONS

The present application claims priority to GB Patent Application No. 2001725.7 entitled "An Intrusion Detector for a Lorry," filed on 7 Feb. 2020. The entire contents of the above-listed application are hereby incorporated by reference for all purposes.

BACKGROUND

For various political, commercial and humanitarian reasons there is a desire to detect intrusion of stowaways into lorries and other freight vehicles.

BRIEF DESCRIPTION OF THE DRAWINGS

The present description will be understood more fully when viewed in conjunction with the accompanying drawings of various examples of intrusion detectors for lorries. The description is not meant to limit the intrusion detectors for lorries to the specific examples. Rather, the specific examples depicted and described are provided for explanation and understanding of intrusion detectors for lorries. Throughout the description the drawings may be referred to as drawings, figures, and/or FIGs.

DETAILED DESCRIPTION

Figure 1:
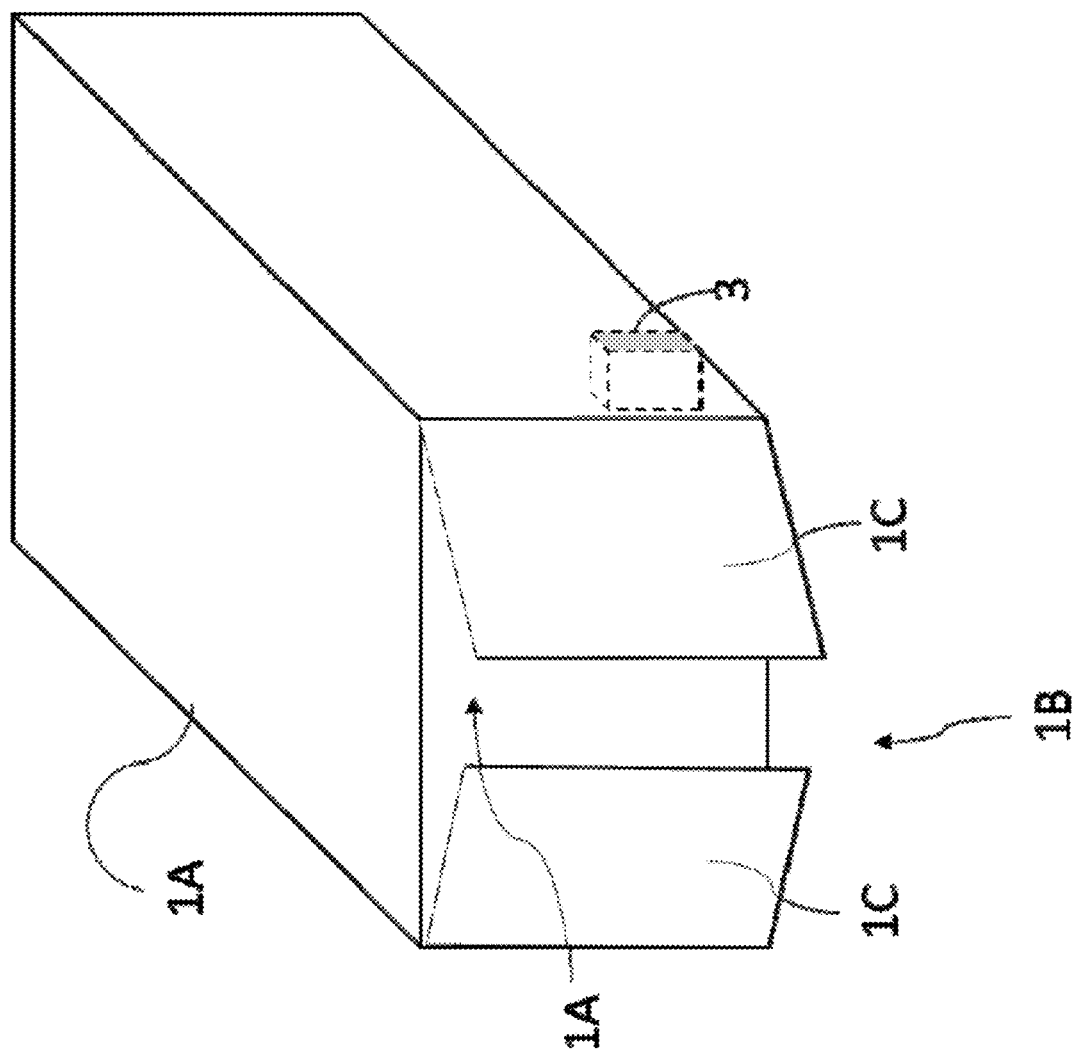
FIG. 1 is a schematic of a trailer for carrying goods having an intrusion sensing device, according to an embodiment.

Intrusion detectors for lorries as disclosed herein will become better understood through a review of the following detailed description in conjunction with the figures. The detailed description and figures provide merely examples of the various embodiments of intrusion detectors for lorries. Many variations are contemplated for different applications and design considerations; however, for the sake of brevity and clarity, all the contemplated variations may not be individually described in the following detailed description. Those skilled in the art will understand how the disclosed examples may be varied, modified, and altered and not depart in substance from the scope of the examples described herein.

The background concentration of $CO_2$ within the atmosphere is currently around 400 parts per million (ppm). When a person enters a typical lorry trailer, the $CO_2$ concentration within the trailer rises to around 460 ppm within around 15 minutes. As a result of the person's respiration. Each additional person present within the trailer increases the concentration by around 60 ppm. Perishable goods such as fruits and vegetables give off $CO_2$ as they perish. In trials the inventors have determined that perishable goods within a lorry trailer can increase $CO_2$ concentration within the trailer from the background concentration to around 2000 ppm. This increase occurs over around a 15 minute period from closing the back of the trailer.

CA3036117 describes an alarm safety system that detects the presence of a person within a confined space by identifying an increase in carbon dioxide ($CO_2$) within the space. As perishable goods increase $CO_2$ concentration significantly more than people the technique of CA3036117 does not allow for confident detection of intruders in trailers carrying perishable goods.

According to a first aspect of intrusion detectors for lorries as described herein, there is provided a method of detecting intrusion of one or more persons into cargo hold of a vehicle carrying goods that emit carbon dioxide the method comprising identifying an intrusion event by detecting a decrease in concentration of carbon dioxide within the cargo hold. For example, the intrusion evident may be identified by detecting a decrease in concentration of carbon dioxide within the cargo hold of at least 400 ppm. A decrease in $CO_2$ can be attributed to unauthorised access being made into the cargo hold as cargo holds typically remain closed during a journey.

Through experimentation the inventors have identified that $CO_2$ concentration within a trailer holding $CO_2$ emitting goods reduces rapidly from an elevated concentration when a trailer door is opened. Therefore the intrusion evident may be identified by detecting a relatively rapid decrease in concentration of carbon dioxide within the cargo hold towards the background atmospheric concentration as compared with the relatively slow increase in carbon dioxide concentration within the cargo hold that occurs as a result of emissions from the goods. An intrusion event may be identified by detecting a decrease in concentration of carbon dioxide within the cargo hold occurring at a rate of at least twenty percent within one second as rates of decrease equal or greater than this was commonly seen in the inventor's experimentation.

The goods may comprise perishable food items such as, for example, fruit and/or vegetables.

The method may include warning of a detected intrusion event and thus may comprise activating an alarm in response to detecting an intrusion event. The alarm may be remote from the vehicle, e.g. at a monitoring station. This is because lorry drivers are often complicit in successful intrusion attempts and thus an alarm that was only for the driver's attention may be of limited benefit. When activated, the alarm may produce an alert, e.g. one or more of a visual, audible and haptic alert. The alert may comprise displaying a message on an electronic device, e.g. a computer screen, for viewing by a superintendent.

The method may comprise identifying the geographic location of the vehicle at about the time the decrease in concentration of carbon dioxide was detected, and comparing that location against expected loading and/or unloading locations for the vehicle; the method further comprises activating the alarm if the geographic location does not substantially correspond with expected loading or unloading locations for the vehicle.

The method may comprise using manifest information to determine whether the cargo hold contains goods that emit $CO_2$; and if the cargo hold is determined to hold goods that emit $CO_2$, using the method in any of variations described above to detect an intrusion event; or if the cargo hold is determined not to be holding goods that emit $CO_2$, identifying an intrusion event by identifying an increase in $CO_2$ level within the cargo hold.

In this way intrusions can be detected irrespective of whether the trailer is carrying goods that emit $CO_2$ or not.

Intrusion detectors for lorries may also be described in terms of apparatus. According to another aspect of intrusion detectors for lorries there is provided apparatus for detecting intrusion of one or more persons in a cargo hold of vehicle carrying goods that emit $CO_2$; the apparatus comprising: a sensor to sense the concentration of $CO_2$ within the cargo hold and output a signal indicative thereof, and detection means arranged to receive and use the signal to identify an intrusion event by detecting a decrease in concentration of $CO_2$ within the cargo hold.

The detection means may be arranged to identify the intrusion event by detecting a decrease in concentration of carbon dioxide within the cargo hold of at least 400 ppm.

The detection means may be arranged to identify the intrusion evident by detecting a relatively rapid decrease in concentration of $CO_2$ within the cargo hold towards the background atmospheric concentration as compared with the relatively slow increase in $CO_2$ concentration within the cargo hold from a baseline concentration caused by emissions from the goods.

The detection means may be arranged to identify the intrusion event by detecting a decrease in concentration of $CO_2$ within the cargo hold occurring at a rate of at least twenty percent within one second. identifying an intrusion event. The apparatus may comprise an alarm mechanism configured to produce an alarm signal in response to receiving the event signal.

The detection means may be arranged to output an event signal in response to identifying an intrusion event. The apparatus may comprise an alarm mechanism configured to produce an alarm signal in response to receiving the event signal.

The alarm mechanism may be located remotely from the vehicle.

The apparatus may comprise a global navigation satellite receiver arranged to output location information to the detection means and the detection means is configured to use the location information to identify an intrusion event by identifying that the geographic location of the vehicle at the time the decrease in concentration of carbon dioxide was detected does not correspond with an expected loading or unloading location for the vehicle. This reduces false alarms as a result of the doors opening during loading and unloading at the starting and ending points of its journey.

The apparatus may comprising a store holding manifest information including an indication of whether there are $CO_2$ emitting goods in the cargo hold; and in which the means for activating the alarm is configured to determine from the manifest whether there are $CO_2$ emitting goods in the cargo hold, and if the means for activating the alarm determines that the cargo hold does not contain goods that emit carbon dioxide, identifying an intrusion event by identifying an increase in carbon dioxide level within the cargo hold.

FIG. 1 illustrates a trailer 1 that defines an interior space 1A for holding cargo and an intrusion sensor device 3 mounted to the trailer 1, e.g. within the interior space for detecting intrusion of one or more persons into the trailer 1.

The trailer 1 includes an access 1B through which cargo can be loaded into and unloaded out from the trailer 1. The access 1B is closable by doors 1C. The trailer 1 may, for example, take the form of a standardised shipping container such as used with intermodal freight transport, that can be mounted on a lorry trailer chassis, or a custom design trailer built on a trailer chassis e.g. in the form of a box or a curtain sided trailer. The trailer 1 may be equipped with a refrigeration system (not shown) in order to control the internal temperature of the interior space 1A. The intrusion sensor device 3 may also be used to detect intrusion within vehicles in which the interior space 1A is defined by the chassis of the vehicle, such as is the case in a van.

Figure 2:
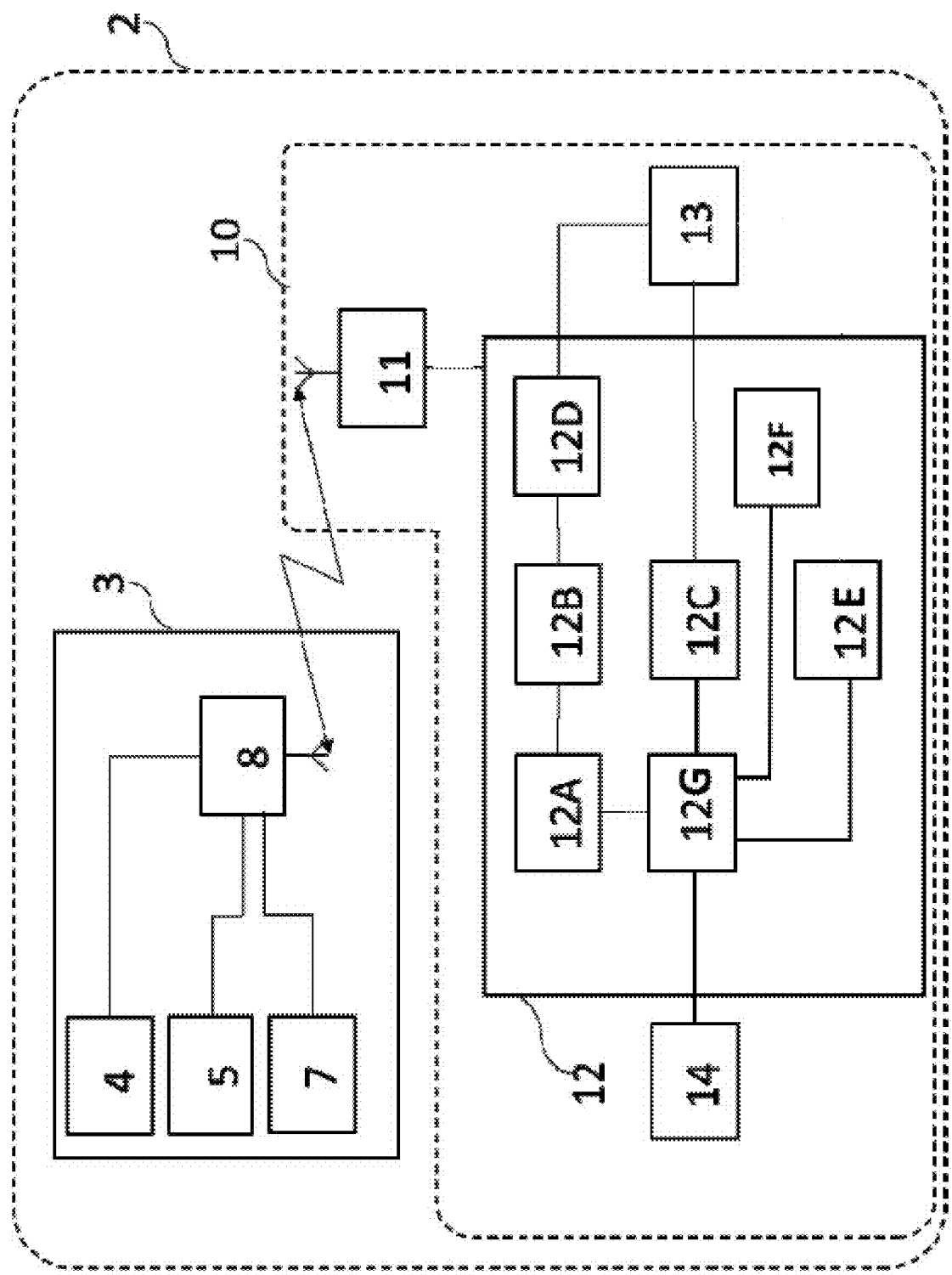
FIG. 2 is a schematic of an intrusion alarm system including the intrusion sensing device of FIG. 1, according to an embodiment.

With reference to FIG. 2, the intrusion sensor device 3 forms part of an intrusion alarm system 2 which also includes a monitoring system 10 located remotely from the intrusion sensor device 3 and trailer 1.

The intrusion alarm system 2 can be configured to detect intrusions in multiple trailers 1 simultaneously. Where so, each trailer 1 is equipped with its own intrusion sensor device 3.

The (or each where there are multiple of) intrusion sensor device 3 includes a carbon dioxide sensor 4, clock 5, global navigation satellite receiver (e.g. GPS receiver) 7, and a wireless transmitter 8.

The carbon dioxide sensor 4 is configured to sense the concentration of carbon dioxide within the interior space 1A and output a signal indicative thereof, hereafter referred to as the $CO_2$ signal.

The wireless transmitter 8 is arranged to transmit the $CO_2$ signal, time data derived from the clock 5, and location information derived from the global navigation satellite receiver 7 to the remote monitoring system 10, e.g. via one or more of a cellular network, satellite network and the internet. The wireless transmitter 8 also transmits identification information (ID) of the intrusion sensor device 3 and/or trailer 1 stored by the intrusion sensor device 3 that is unique to the device-trailer combination.

The remote monitoring system 10 comprises a receiver 11, an intrusion detector 12, a store 13 that holds vehicle information, and an alarm 14.

The intrusion detector 12 includes the functions of a: $CO_2$ analyser 12A; configuration selector 12B; location comparator 12C; manifest lookup 12D; speed determiner 12E; motion analyser 12F and event signal generator 12G.

The functions of the intrusion detector 12 may be realised in a combination of hardware and software. Any kind of computer system is suitable. A typical combination of hardware and software could be a general purpose computer system with a computer program that, when being loaded and executed, controls the computer system such that it carries out the methods described herein.

The vehicle information held in store 13, which may be in the form of a table, comprises an entry for each trailer 1 that carries an intrusion sensor device 3. Each entry includes the unique ID of the intrusion sensor device 3 or trailer 1; start and destination location information for one or more journeys and, for each journey, manifest information including an indicator of whether the trailer is carrying, for that journey, goods that emit $CO_2$. Where the vehicle information includes information for multiple journeys it may also hold time information relating to each journey, e.g. one or more of an expected start and finish time for each journey.

The receiver 11 is arranged to receive the $CO_2$ signal, time data, location information and ID information transmitted by the transmitter 8 and forward it to the intrusion detector 12.

The $CO_2$ analyser 12A of the intrusion detector 12 identifies a possible intrusion event from the received $CO_2$ signal and, depending on its configuration, time data to identify an intrusion event from changes in carbon dioxide concentration within the interior space 1A.

In response to determining an intrusion event, the event signal generator 12G outputs an event signal to the alarm 14 which in response generates one or more of an audible, haptic and visual alert to warn a superintendent of the remote monitoring system of an intrusion.

The alert may comprise an electronic message (e.g. e-mail, instant message or SMS), for display on an electronic device, e.g. computer and/or phone. Where the alert comprises a message, the message may include information including the ID of the intrusion sensor device 3 and/or trailer 1 and location information of the trailer 1.

Upon receiving data from the intrusion sensor device 3, the intrusion detector 12 looks up the received ID in the vehicle journey information held in store 13 and the location comparator 12C compares the trailer's location as indicated by the location information with the start and destination locations of the relevant journey (if more than one is held) in order to determine whether the trailer 1 is at the start or destination of said journey. If it is determined that the trailer 1 is at either the start or destination location the event signal generator 12G is caused to not generate an event signal in order to avoid false alarms as it is expected that the trailer's interior would be accessed legitimately at these locations.

This may be implemented by, for example, the location comparator 12C sending a signal to the event signal generator 12C that causes the event signal generator 12C to ignore any output from the $CO_2$ analyser 12A, or by sending a signal to prevent the $CO_2$ analyser from operating.

The $CO_2$ analyser 12A is configured by configuration selector 12B to operate in one of two ways depending on the nature of the goods held within the trailer 1. The manifest lookup 12D looks up manifest information from the vehicle journey information in store 13 to determine whether the trailer 1 is carrying $CO_2$ emitting goods and passes this to the configuration selector 12B. If the trailer 1 is carrying $CO_2$ emitting goods the configuration selector 12B configures the $CO_2$ analyser 12A to analyse the $CO_2$ signals and time signals in order to identify any decrease in $CO_2$ concentration within the interior space 1A occurring at a rate of at least twenty percent within a second. In response to identifying such an occurrence, the event signal generator 12G is caused to emit the event signal to the alarm 14.

If the manifest information indicates that the trailer 1 is not holding $CO_2$ emitting goods then configuration selector 12B configures the analyser 12A to identify any increase in $CO_2$ concentration within the interior space 1A and in response to produce an event signal to the alarm 14. To reduce false positives, the intrusion detector 12 is configured to identify an increase in $CO_2$ concentration over atmospheric concentration above a threshold amount, e.g. 60 ppm.

An increase in $CO_2$ concentration within the trailer 1 is expected either because the interior space holds $CO_2$ emitting goods and/or humans that have stowed away within the trailer 1.

A rapid drop in $CO_2$ is expected as a result of $CO_2$ concentration within the trailer 1 having risen significantly above the atmospheric concentration, e.g. due to the presence of $CO_2$ emitting goods within the space 1A, before the interior space 1A being opened to the atmosphere through the opening of doors 1C which would allow $CO_2$ to escape quickly. For example, in a trailer carrying fresh fruit or vegetables, the $CO_2$ concentration within the trailer may be expected to rise to an elevated level of around 2000 ppm and would be expected to drop by at least 400 ppm equating to 20% of 2000 ppm, within a second as a result of the trailer door 1C opening.

To further reduce the instances of false positives, system a speed determiner 12E is configured to use the location information and time information to determine the speed of the vehicle and to prevent the generator 12G outputting an event signal if the vehicle is travelling above a threshold speed, e.g. 10 miles per hour, as stowaways are unlikely to be able to access the vehicle when it is travelling at speed.

The intrusion device 3 may include an impact and/or motion sensor (not shown) to detect an impact or motion of the intrusion device tamper detection. The output of the impact or motion sensor is received transmitted by the transmitter 8 for receipt by the motion analyser 12F which determines from the output of the impact and/or motion sensor an attempt to tamper with the intrusion device by identifying impact or motion of the intrusion device that matches an impact or motion profile.

The intrusion device 3 may include a light sensor (not shown). The output of the light sensor may be used, together with the $CO_2$ signal by the intrusion detector 12 to detect an intrusion event, a sudden increase in brightness being indicative that a door of the trailer has been opened.

The light sensor, speed determiner, and motion analyser are all optional features.

In an alternative embodiment the function of the $CO_2$ analyser may be provided by the intrusion sensor device 3.

In such an arrangement the carbon dioxide sensor 4 is configured to sense the concentration of carbon dioxide within the interior space 1A and output a signal indicative thereof directly to the $CO_2$ analyser. The $CO_2$ analyse uses the output from the sensor 4 together with the clock signal to identify an intrusion event as a result of determining either: i) decrease in $CO_2$ concentration within the interior space 1A of at least thirty percent occurring within a second; or ii) an increase in $CO_2$ concentration within the interior space 1A.

In response to determining a possible intrusion event, the $CO_2$ analyse outputs an event detection signal that is transmitted by the wireless transmitter 8 to the remote monitoring system 10.

The detection signal includes identification information (ID) of the intrusion sensor device 3 and/or trailer 1, location information of the trailer 1 derived from the global navigation satellite receiver 7, and an indicator of the cause that triggered the detection signal, i.e. either cause i) or ii) above. The remote monitoring system 10 uses the indicator of cause and the manifest information to determine whether to activate the alarm 14 upon receipt of an event detection signal. For example, if the detection signal was activated as a result of cause ii), the alarm 14 would not be activated if the manifest information indicated that the trailer held $CO_2$ producing goods.

The intrusion detectors and systems described herein may have application beyond lorry trailers to other freight vehicles, such as for example, goods wagons of freight trains.

A feature illustrated in one of the figures may be the same as or similar to a feature illustrated in another of the figures. Similarly, a feature described in connection with one of the figures may be the same as or similar to a feature described in connection with another of the figures. The same or similar features may be noted by the same or similar reference characters unless expressly described otherwise. Additionally, the description of a particular figure may refer to a feature not shown in the particular figure. The feature may be illustrated in and/or further described in connection with another figure.

Elements of processes (i.e. methods) described herein may be executed in one or more ways such as by a human, by a processing device, by mechanisms operating automatically or under human control, and so forth. Additionally, although various elements of a process may be depicted in the figures in a particular order, the elements of the process may be performed in one or more different orders without departing from the substance and spirit of the disclosure herein.

The foregoing description sets forth numerous specific details such as examples of specific systems, components, methods and so forth, in order to provide a good understanding of several implementations. It will be apparent to one skilled in the art, however, that at least some implementations may be practiced without these specific details. In other instances, well-known components or methods are not described in detail or are presented in simple block diagram format in order to avoid unnecessarily obscuring the present implementations. Thus, the specific details set forth above are merely exemplary. Particular implementations may vary from these exemplary details and still be contemplated to be within the scope of the present implementations.

Related elements in the examples and/or embodiments described herein may be identical, similar, or dissimilar in different examples. For the sake of brevity and clarity, related elements may not be redundantly explained. Instead, the use of a same, similar, and/or related element names and/or reference characters may cue the reader that an element with a given name and/or associated reference character may be similar to another related element with the same, similar, and/or related element name and/or reference character in an example explained elsewhere herein. Elements specific to a given example may be described regarding that particular example. A person having ordinary skill in the art will understand that a given element need not be the same and/or similar to the specific portrayal of a related element in any given figure or example in order to share features of the related element.

It is to be understood that the foregoing description is intended to be illustrative and not restrictive. Many other implementations will be apparent to those of skill in the art upon reading and understanding the above description. The scope of the present implementations should, therefore, be determined with reference to the appended claims, along with the full scope of equivalents to which such claims are entitled.

The foregoing disclosure encompasses multiple distinct examples with independent utility. While these examples have been disclosed in a particular form, the specific examples disclosed and illustrated above are not to be considered in a limiting sense as numerous variations are possible. The subject matter disclosed herein includes novel and non-obvious combinations and sub-combinations of the various elements, features, functions and/or properties disclosed above both explicitly and inherently. Where the disclosure or subsequently filed claims recite "a" element, "a first" element, or any such equivalent term, the disclosure or claims is to be understood to incorporate one or more such elements, neither requiring nor excluding two or more of such elements.

As used herein "same" means sharing all features and "similar" means sharing a substantial number of features or sharing materially important features even if a substantial number of features are not shared. As used herein "may" should be interpreted in a permissive sense and should not be interpreted in an indefinite sense. Additionally, use of "is" regarding examples, elements, and/or features should be interpreted to be definite only regarding a specific example and should not be interpreted as definite regarding every example. Furthermore, references to "the disclosure" and/or "this disclosure" refer to the entirety of the writings of this document and the entirety of the accompanying illustrations, which extends to all the writings of each subsection of this document, including the Title, Background, Brief description of the Drawings, Detailed Description, Claims, Abstract, and any other document and/or resource incorporated herein by reference.

As used herein regarding a list, "and" forms a group inclusive of all the listed elements. For example, an example described as including A, B, C, and D is an example that includes A, includes B, includes C, and also includes D. As used herein regarding a list, "or" forms a list of elements, any of which may be included. For example, an example described as including A, B, C, or D is an example that includes any of the elements A, B, C, and D. Unless otherwise stated, an example including a list of alternatively-inclusive elements does not preclude other examples that include various combinations of some or all of the alternatively-inclusive elements. An example described using a list of alternatively-inclusive elements includes at least one element of the listed elements. However, an example described using a list of alternatively-inclusive elements does not preclude another example that includes all of the listed elements. And, an example described using a list of alternatively-inclusive elements does not preclude another example that includes a combination of some of the listed elements. As used herein regarding a list, "and/or" forms a list of elements inclusive alone or in any combination. For example, an example described as including A, B, C, and/or D is an example that may include: A alone; A and B; A, B and C; A, B, C, and D; and so forth. The bounds of an "and/or" list are defined by the complete set of combinations and permutations for the list.

Where multiples of a particular element are shown in a FIG., and where it is clear that the element is duplicated throughout the FIG., only one label may be provided for the element, despite multiple instances of the element being present in the FIG. Accordingly, other instances in the FIG. of the element having identical or similar structure and/or function may not have been redundantly labeled. A person having ordinary skill in the art will recognize based on the disclosure herein redundant and/or duplicated elements of the same FIG. Despite this, redundant labeling may be included where helpful in clarifying the structure of the depicted examples.

The Applicant(s) reserves the right to submit claims directed to combinations and sub-combinations of the disclosed examples that are believed to be novel and non-obvious. Examples embodied in other combinations and sub-combinations of features, functions, elements and/or properties may be claimed through amendment of those claims or presentation of new claims in the present application or in a related application. Such amended or new claims, whether they are directed to the same example or a different example and whether they are different, broader, narrower or equal in scope to the original claims, are to be considered within the subject matter of the examples described herein.

The invention claimed is:

1. A method of detecting intrusion of one or more persons into a cargo hold of a vehicle carrying goods that emit carbon dioxide, comprising:
   identifying an intrusion event by detecting a decrease in concentration of carbon dioxide of at least thirty percent within one second within the cargo hold.

2. A method according to claim 1, wherein the goods cause a relatively slow increase in carbon dioxide concentration within the space from a baseline concentration, and in which the intrusion evident is identified by detecting a relatively rapid decrease in concentration of carbon dioxide within the cargo hold towards the baseline concentration.

3. A method according to claim 2 wherein the intrusion event is identified by detecting a decrease in concentration of carbon dioxide within the cargo hold of at least thirty percent within one second.

4. A method according to claim 1, comprising activating an alarm in response to detecting an intrusion event.

5. A method according to claim 4, wherein the alarm is located remote from the vehicle.

6. A method according to claim 1, wherein identifying intrusion event comprising identifying that the geographic location of the vehicle at the time the decrease in concentration of carbon dioxide was detected does not correspond with an expected loading or unloading location for the vehicle.

7. A method of detecting intrusion of one or more persons in a cargo hold of a vehicle, comprising:
- determining from a manifest whether the cargo hold is holding goods that emit carbon dioxide; and
- in response to determining the cargo hold holds goods that emit carbon dioxide:
  - detecting a relatively rapid decrease in concentration of carbon dioxide within the cargo hold towards the baseline concentration;
  - activating an alarm; and
- in response to determining the cargo hold is not holding goods that emit carbon dioxide, warning of an intrusion event by identifying an increase in carbon dioxide level within the cargo hold.

8. A system for detecting intrusion of one or more persons in a cargo hold of a vehicle carrying goods that emit carbon dioxide; the system comprising:
- a sensor to sense the concentration of carbon dioxide within the cargo hold and output a signal indicative thereof, and detection means arranged to receive the signal from the sensor and to identify an intrusion event by detecting a relatively rapid decrease in concentration of carbon dioxide within the cargo hold towards the baseline concentration wherein:
  - the goods cause a relatively slow increase in carbon dioxide concentration within the cargo hold from a baseline concentration, and in which the detection means is arranged to identify the intrusion evident by detecting a relatively rapid decrease in concentration of carbon dioxide within the cargo hold towards the baseline concentration, and
  - the sensor is arranged to identify the intrusion event by detecting a decrease in concentration of carbon dioxide within the cargo hold of at least twenty percent within one second.

9. A system according to claim 8, wherein the detection means is arranged to output an event signal in response to identifying an intrusion event and the system comprising an alarm mechanism configured to activate to produce an alarm signal in response to receiving the event signal.

10. A system according to claim 9 comprising a store holding manifest information including an indication of whether there are CO2 emitting goods in the cargo hold, wherein the means for activating the alarm is configured to determine from the manifest whether there are CO2 emitting goods in the cargo hold, and if the means for activating the alarm determines that the cargo hold does not contain goods that emit carbon dioxide, identifying an intrusion event by identifying an increase in carbon dioxide level within the cargo hold.

11. A system according to claim 9, wherein the alarm is located remote from the vehicle.

12. A system according to claim 8 comprising a navigation satellite receiver and the detection means uses an output of the navigation satellite receive to identify an intrusion event by identifying that the geographic location of the vehicle at the time the decrease in concentration of carbon dioxide was detected does not correspond with an expected loading or unloading location for the vehicle.

* * * * *